US007781458B2

(12) United States Patent
Lacal Sanjuán et al.

(10) Patent No.: US 7,781,458 B2
(45) Date of Patent: Aug. 24, 2010

(54) DERIVATIVES OF PYRIDINE AND QUINOLINE

(75) Inventors: Juan Carlos Lacal Sanjuán, Madrid (ES); Joaquin Campos Rosa, Granada (ES); Miguel Ángel Gallo Mezo, Granada (ES); Antonio Espinosa Úbeda, Granada (ES)

(73) Assignees: Consejo Superior de Investigaciones Cientificas, Madrid (ES); Universidad de Granada, Granada (ES)

( * ) Notice: Subject to any disclaimer, the term of this patent is extended or adjusted under 35 U.S.C. 154(b) by 907 days.

(21) Appl. No.: 10/597,095

(22) PCT Filed: Jan. 11, 2005

(86) PCT No.: PCT/ES2005/070002

§ 371 (c)(1),
(2), (4) Date: Sep. 29, 2006

(87) PCT Pub. No.: WO2005/068429

PCT Pub. Date: Jul. 28, 2005

(65) Prior Publication Data

US 2007/0185170 A1 Aug. 9, 2007

(30) Foreign Application Priority Data

Jan. 14, 2004 (ES) .................. 200400072

(51) Int. Cl.
*A61K 31/44* (2006.01)
*C07D 215/38* (2006.01)
*C07D 213/74* (2006.01)

(52) U.S. Cl. ............... 514/313; 514/332; 546/159; 546/255

(58) Field of Classification Search ............ None
See application file for complete search history.

(56) References Cited

U.S. PATENT DOCUMENTS 4,206,215 A * 6/1980 Bailey ............... 514/332

FOREIGN PATENT DOCUMENTS

| EP | 56766 A | 7/1982 |
| EP | 326331 A | 8/1989 |
| ES | 2117950 | 8/1998 |
| JP | 37007238 | 7/1962 |

OTHER PUBLICATIONS

Campos, "Anticancer Bisquaternary Hetercyclic Compounds: A Racional Design," Farmaco., vol. 58, No. 3, (2003), pp. 221-229.
Conejo-Garcia, et al., "Choline Kinase Inhibitory Effect and Antiproliferative Activity of New 1,1',1"-(Benzene-1,3,5-Triylmethlyene) Tris {4-[(Disubstituted) Amino] Pyridinium} Tribromides," European Journal of Medicinal Chemistry, vol. 38, No. 1, (2003), pp. 109-116.
Campos, "Quantitative Structure-Activity Relationships for a Series of Symmetrical Bisquaternary Anticancer Compounds," Bioorganic & Medicinal Chemistry, vol. 10, No. 7, (2002), pp. 2215-2231.
Galanakis, "Synthesis and Quantitative Structure-Activity. Relationship of Dequalinium Analogs as K+ Channel Blockers: Investigations on the Role of the Substituent at Position 4 of the Quinoline Ring," Journal of Medicinal Chemistry, vol. 38, No. 18, (1995), pp. 3536-3546.

* cited by examiner

*Primary Examiner*—Zinna N Davis
(74) *Attorney, Agent, or Firm*—Tristan A. Fuierer; Moore & Van Allen, PLLC

(57) ABSTRACT

The invention provides compounds of formula I blocking phosphorylcholine biosynthesis by means of the selective blocking of the choline kinase enzyme in tumor cells or in cells affected by parasitic infection and therefore being applicable in the treatment of tumors and parasitic diseases or diseases produced by viruses and fungi in animals, including human beings; as well as to a method for preparing the compounds of the invention and certain intermediates of said method.

14 Claims, No Drawings

DERIVATIVES OF PYRIDINE AND QUINOLINE

CROSS-REFERENCE TO RELATED APPLICATIONS

This application is filed under the provisions of 35 U.S.C. §371 and claims the priority of International Patent Application No. PCT/ES2005/070002 on Jan. 11, 2005, which in turn claims priority of Spanish Patent Application No. P200400072 filed on Jan. 14, 2004.

FIELD OF THE INVENTION

The invention generally relates to compounds blocking phosphorylcholine biosynthesis by means of the selective blocking of the choline kinase enzyme in tumor cells or in cells affected by parasitic infection and therefore being applicable in the treatment of tumors and parasitic diseases or diseases produced by viruses, bacteria and fungi in animals including human beings; as well as to a method for preparing the compounds of the invention and certain intermediates of said method.

BACKGROUND OF THE INVENTION

Choline kinase is the first enzyme in the Kennedy or phosphatidylcholine (PC) synthesis pathway and phosphorylates choline to phosphorylcholine (PCho) using adenosine 5'-triphosphate (ATP) as a phosphate group donor [Kent, C. *Prog. Lipid Res.*, 29, 87-105 (1990); Kennedy, E. P. *Fed. Proc.*, 20, 934-940 (1961)]. Ras genes form a family called oncogenes, which have been widely studied because they are activated in 25-30% of all human tumors and in some of them in 90% [Bos, J L. *Cancer Res* 49, 4682-4689 (1989); Kiaris, H., Spandidos, D. A. *Int. J. Oncol.*, 413-421 (1995)]. Ras proteins play an important role in intracellular signal transmission due to their involvement in regulating cell proliferation, terminal differentiation and senescence [Abdellatif, M., MacLellan, W. R.; Schneider, M. D. *J. Biol. Chem.*, 269, 15423-15426 (1994); Wiesmüller, L., Wittinghofer, F. *Cell Signal.*, 6, 247-267 (1994); Barbacid, M. *Eur. J. Clin. Invest.*, 20, 225-235 (1990); Hahn & Weinberg *Nat. Rev. Cancer*, 2: 331 (2002); Wright & Shay *Nat. Biotech*, 20: 682 (2002); Drayton & Peters *Curr. Op. Gen. Dev*, 12:98 (2002)]. The transformation mediated by various oncogenes, amongst which ras oncogenes stand out, induces high levels of choline kinase activity, resulting in an abnormal increase in the intracellular levels of its product, PCho [Lacal et al., *Nature* 330, 269-272 (1987); Lacal J. C. *Mol. Cell. Biol.* 10, 333-340 (1990); Teegarden, D., Taparowsky, E. J., Kent, C. *J. Biol. Chem.* 265, 6042-6047 (1990); Ratnam, S.; Kent, C. *Arch. Biochem. Biophys.* 323, 313-322 (1995); Ramírez de Molina, A., Rodríguez-González, A., Peñalva, V., Lucas, L., Lacal, J. C. *Biochem. Biophys. Res. Commun.* 285, 873-879 (2001); Ramírez de Molina, A., Peñalva, V.; Lucas, L., Lacal, J. C. *Oncogene* 21, 937-946 (2002)]. Supplementary facts support the role of ChoK in the generation of human tumors because studies using nuclear magnetic resonance (NMR) techniques have shown high levels of PCho in human tumor tissues with respect to normal tissues, including, among others, breast, colon, lung and prostate tumors [Ruiz-Cabello, J., Cohen, J. S. *NMR Biomed.* 5, 226-233 (1992); de Certaines, J. D., Larsen, V. A., Podo, F., Carpinelli, G., Briot, O., Henriksen, O. *NMR Biomed.* 6, 345-365 (1993); Smith, T. A. D., Bush, C., Jameson, C., Titley, J. C., Leach, M. O., Wilman, D. E. V., McCready, V. R. *NMR Biomed.* 6, 318-323 (1993)]. It is common knowledge that ras is one of the most profoundly studied oncogenes in human carcinogenesis and that ChoK inhibition has shown to be a new and efficient antitumor strategy in cells transformed by oncogenes [Cuadrado, A., Carnero, A., Dolfi, F., Jiménez, B., Lacal, J. C. *Oncogene*, 8, 2959-2968 (1993); Jiménez, B., del Peso, L., Montaner, S., Esteve, P. Lacal, J. C. *J. Cell Biochem.*, 57, 141-149 (1995); Hernández-Alcoceba, R., Saniger, L., Campos, J., Núñez, M. C., Khaless, F., Gallo, M. Á., Espinosa, A., Lacal, J. C. *Oncogene*, 15, 2289-2301 (1997)]. These first observations were later extrapolated in vivo in nude mice [Hernández-Alcoceba, R., Fernández, F., Lacal, J. C. *Cancer Res.* 59, 3112-3118 (1999)]. The research on ChoK inhibitors has identified Hemicholinium-3 (HC-3) as a relatively powerful and selective blocking agent [Cuadrado A., Carnero A., Dolfi F., Jiménez B. and Lacal J. C. *Oncogene* 8, 2959-2968 (1993); Jiménez B., del Peso L., Montaner S., Esteve P. and Lacal J. C. *J. Cell Biochem.* 57, 141-149 (1995); Hernández-Alcoceba, R., Saniger, L., Campos, J., Núñez, M. C., Khaless, F., Gallo, M. Á., Espinosa, A., Lacal, J. C. *Oncogene*, 15, 2289-2301 (1997)]. This choline homologue with a biphenyl structure has been used to design new antitumor drugs. Since HC-3 is a powerful respiratory paralyzing agent, it is not a good candidate for its clinical use. The synthesis of several derivatives has been based on structural modifications of HC-3 improving the ChoK inhibitory activity and suppressing its toxic effects. The inhibitory effect produced by bisquaternized symmetrical compounds on proliferation has been correlated with the ability to induce PCho production in whole cells [Hernández-Alcoceba, R., Saniger, L., Campos, J., Núñez, M. C., Khaless, F., Gallo, M. Á., Espinosa, A., Lacal, J. C. *Oncogene*, 15, 2289-2301 (1997) and ES 2 117 950]. When the 1,2-ethylene-p-(bibenzyldimethyl-diyl) residue was used as spacer between the two cationic pyridinium heads substituted in position 4 [Campos, J., Núñez, M. C., Rodríguez, V., Gallo, M. Á., Espinosa, A. *Bioorg. & Med. Chem. Lett.* 10, 767-770 (2000)], the structures were evaluated by their ability to inhibit the isolated ChoK (in ex vivo conditions) [Lacal J. C. *IDrugs* 4: 419-426 (2001)]. The 4-NR$_2$ group provided a considerable contribution and it was proposed [Campos, J., Núñez, M. C., Rodríguez, V., Gallo, M. Á., Espinosa, A. *Bioorg. & Med. Chem. Lett.* 10, 767-770 (2000)] that the role of this group is electronic, by delocalization of the positive charge. The increase in ChoK activity in various human breast carcinomas has been published [Ramírez de Molina, A., Gutiérrez, R., Ramos, M. A., Silva, J. M., Silva, J., Sánchez, J. J., Bonilla, F., Lacal, J. C. *Oncogene* 21, 4317-4322 (2002)]. It has recently been reported that ChoK alteration is a frequent event in some human tumors such as lung, colorectal and prostate tumors [Ramírez de Molina, A., Rodríguez-González, A., Gutiérrez, R., Martínez-Piñero, L., Sánchez, J. J., Bonilla, F., Rosell, R., Lacal, J. C. *Biochem. Biophys. Res. Commun.* 296, 580-583 (2002)].

The bisquaternized pyridinium derivatives described in the state of the art and particularly in patent ES 2 117 950, show, however, high levels of toxicity, limiting their extended therapeutic application.

Therefore, in the state of the art there is a need to develop compounds having an activity blocking phosphorylcholine biosynthesis in tumor cells or in processes produced by parasitic, viral, bacterial or fungal infection, and, at the same time, having low levels of toxicity.

The authors of the present invention have discovered, after diligent research, that certain modifications in the structure of the compounds described in the state of the art and particularly in patent ES 2 117 950, have an unexpectedly and

BRIEF DESCRIPTION OF THE INVENTION

Therefore, the invención provides as its first object a family of compounds having formula I,

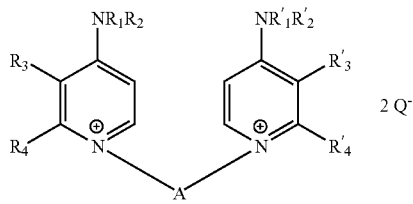

the structure of which is characterized by having two N-aryl-aminopyridinium groups joined by a spacer. In addition to acting as blocking agents of phosphorylcholine biosynthesis, by means of selectively blocking the choline kinase enzyme in tumor cells or potentially in processes produced by parasitic, viral, bacterial or fungal infections, the compounds of this family have low levels of toxicity.

In a second object, the invention provides the use of the compounds of formula I in medicine.

An additional object of the present invention consists of providing pharmaceutical formulations comprising at least one compound of formula I.

The invention provides, in another object, a method for preparing the compounds of formula I.

Finally, the invention provides the compounds of formula VII participating as starting compounds in the method for preparing compounds of formula I.

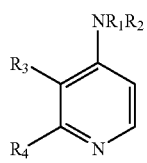

DETAILED DESCRIPTION OF THE INVENTION

In its first object, the invention provides a family of compounds corresponding to general formula I:

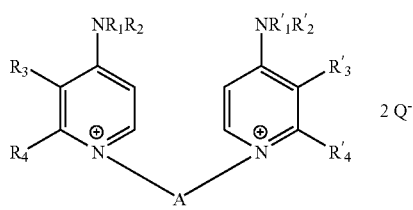

where $Q^-$ represents the conjugate base of a pharmaceutically suitable organic or inorganic acid;

$R_1$ and $R'_1$ represent, independently of each other, a radical selected from the group formed by H and $C_{1-6}$ alkyl optionally substituted by trifluoromethyl, hydroxyl or alkoxyl;

$R_2$ and $R'_2$ represent, independently of each other, an aryl radical optionally substituted by halogen, trifluoromethyl, hydroxyl, $C_{1-6}$ alkyl, amino or alkoxyl;

$R_3$ and $R'_3$ represent, independently of each other, either a radical selected from the group formed by H, halogen, trifluoromethyl, hydroxyl, amino, alkoxyl and $C_{1-6}$ alkyl optionally substituted by trifluoromethyl, hydroxyl, amino or alkoxyl, or together with $R_4$ and $R'_4$ respectively, and independently of each other, a —CH=CH—CH=CH— radical optionally substituted by halogen, trifluoromethyl, hydroxyl, $C_{1-6}$ alkyl, amino or alkoxyl;

$R_4$ and $R'_4$ represent, independently of each other, either a radical selected from the group formed by H and $C_{1-6}$ alkyl optionally substituted by halogen, trifluoromethyl, hydroxyl, amino or alkoxyl, or together with $R_3$ and $R'_3$ respectively, and independently of each other, a —CH=CH—CH=CH— radical optionally substituted by halogen, trifluoromethyl, hydroxyl, $C_{1-6}$ alkyl, amino or alkoxyl; and A represents a spacer group.

In addition to acting as blocking agents of phosphorylcholine biosynthesis by means of selectively blocking the choline kinase enzyme in tumor cells or in cells affected by parasitic infection, the compounds belonging to this family are characterized by having levels of toxicity lower than those of compounds of similar structure known in the state of the art. This feature of the compounds of the invention is shown in the examples given below.

In view of the present invention, spacer group "A" is understood as any divalent organic structure acting as a joining link between the two pyridinium groups present in the structure defined by formula I. In a particular embodiment of the invention, the spacer A has a structure according to one of the formulas II, III, IV, V and VI. These formulas represent radicals; in them, the line—at the ends represents a bond, and not a methyl group.

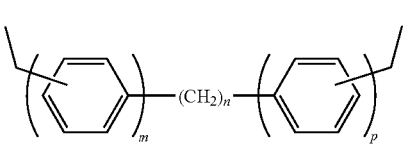

where m, n and p represent integers which can have the following values: m=0, 1; n=0, 1-10; p=0, 1; with the condition that m, n and p do not take the value of zero at the same time.

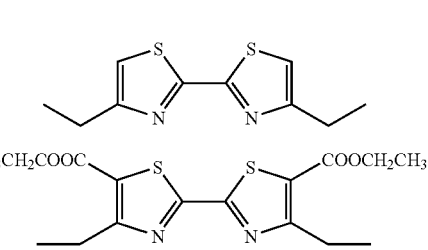

-continued

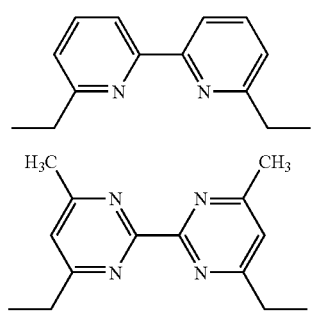

According to the present invention, the radicals $R_1$ and $R'_1$, $R_2$ and $R'_2$, as well as $R_3$ and $R_4$, $R'_3$ and $R'_4$ can represent different radicals or the same radicals, giving rise to asymmetric or symmetric compounds.

In a particular embodiment of the invention, the radicals $R_2$ and $R'_2$ represent, independently of each other, a phenyl radical optionally substituted by halogen, trifluoromethyl, hydroxyl, $C_{1-6}$ alkyl, amino and alkoxyl. In another particular embodiment of the invention, the radicals $R_1$ and $R'_1$ represent a methyl radical, whereas the radicals $R_2$ and $R'_2$ represent independently of each other a phenyl radical optionally substituted by one or more halogen substituents. In a third particular embodiment, both the radicals $R_3$ and $R_4$ and the radicals $R'_3$ and $R'_4$ together represent, although independently of each other, a —CH=CH—CH=CH— radical optionally substituted by one or more halogen substituents.

The preferred compounds of the invention are shown in the following table I:

TABLE I

| N° | $R_3, R_4$* | $NR_1R_2$ | A | Code |
|---|---|---|---|---|
| 1 | H, H | —N(Me)—C6H4—Cl | 1,3-bis(methylene)benzene | ACG560B |
| 2 | H, H | —N(Me)—C6H5 | 3,3'-bis(methylene)biphenyl | ACG416B |
| 3 | H, H | —N(Me)—C6H4—Cl | 3,3'-bis(methylene)biphenyl | ACG548B |
| 4 | H, H | —N(Me)—C6H3(Cl)2 (3,5-dichloro) | 3,3'-bis(methylene)biphenyl | ACG604A |
| 5 | —(CH=CH)2— | —N(Me)—C6H4—Cl | 3,3'-bis(methylene)biphenyl | RSM964A |
| 6 | —C5H=C6H—C7Cl=C8H— | —N(Me)—C6H4—Cl | 3,3'-bis(methylene)biphenyl | RSM820C |

TABLE I-continued

| N° | R$_3$, R$_4$* | NR$_1$R$_2$ | A | Code |
|---|---|---|---|---|
| 7 | —(CH=CH)$_2$— | —N(Me)—C$_6$H$_4$—Cl | —CH$_2$—C$_6$H$_4$—C$_6$H$_4$—CH$_2$— | RSM932A |
| 8 | C$^5$H=C$^6$H—<br>C$^7$Cl=C$^8$H— | —N(Me)—C$_6$H$_4$—Cl | —CH$_2$—C$_6$H$_4$—C$_6$H$_4$—CH$_2$— | RSM824B |
| 9 | —(CH=CH)$_2$— | —N(Me)—C$_6$H$_4$—Cl | —CH$_2$—C$_6$H$_4$—(CH$_2$)$_2$—C$_6$H$_4$—CH$_2$— | RSM936A |
| 10 | —C$^5$H=C$^6$H—<br>C$^7$Cl=C$^8$H— | —N(Me)—C$_6$H$_4$—Cl | —CH$_2$—C$_6$H$_4$—(CH$_2$)$_2$—C$_6$H$_4$—CH$_2$— | RSM828B |

*R$_3$ and R$_4$ can mean either each one is hydrogen or both form a single radical.

Finally, in a preferred embodiment of the invention, the conjugate base of pharmaceutically suitable organic or inorganic acid Q represents Br (bromide) or F$_6$P (hexafluorophosphate).

The compounds of the invention have a selective effect on signaling pathways necessary for transforming certain oncogenes which do not affect normal cells with the same intensity and therefore, leave a sufficient margin for greater efficacy in antitumor treatment.

On the other hand, the biological assays carried out by the authors of the invention allow extending this type of activity to antiviral, antiparasitic or antifungal activity because it is known that several parasites like *Plasmodium falciparum* or *Trypanosoma cruzi*, several viruses such as adenovirus, bacteria such as *Streptococcus pneumoniae* and fungi like *Candida albicans* require the metabolic pathway of phosphatidylcholine synthesis through choline kinase in order to complete their infective cycles in humans and animals. In this sense, the background in literature supports the role of ChoK in the intracellular metabolism in certain nucleosides in Hep-G2 cells [Martin, L. T.; Faraj, A.; Schinazi, R. F.; Gosselin, G.; Mathe, C.; Imbach, J.-L.; Sommadossi, J.-P. *Biochemical Pharmacology*, 53, 75-87 (1997)], the use of ChoK as an enzymatic marker in parasitic diseases [Wunderlich, F.; Helwig, M.; Schillinger, G.; Vial, H.; Philippot, J.; Speth, V. *Molecular and Biochemical Parasitology*, 23, 103-115 (1987); Ancelin, M. L.; Vial, H. J. *Biochimica et Biophysica Acta (BBA)—Lipids and Lipid Metabolism*, 875, 52-58 (1986)], and the participation of ChoK in the biosynthesis of important phospholipids in viruses [Balakivera L., Schoen G., Thouvenin E., Chroboczek J. *J. Virol.* 77:4858-4866 (2003)], bacteria [Whiting G C, Gillespie S H. *FEMS Microbiol Lett.* 138:141-145 (1996)] and fungi [Mago N, Khuller G K. *J Med Vet Mycol.* 28:355-362 (1990)]); Mago N, Khuller G K. *J Med Vet Mycol.* 28:355-362 (1990)]. All these studies support that ChoK inhibition could have important therapeutic consequences in curing the diseases mentioned hereinbefore.

Therefore, in a second object, the invention provides the use of the compounds of formula I in medicine. Specifically, the compounds of formula I are claimed for their use in medicine. In a particular embodiment, the invention provides the compounds of formula I for the treatment of cancer, preferably, breast, lung, colorectal and pancreatic cancer. In another particular embodiment, the invention provides the compounds of formula I for the treatment of viral disease, preferably those caused by Adenovirus; as well as for antiparasitic treatment, preferably for those diseases caused by *Plasmodium* or *Trypanosoma*; antibacterial treatment, preferably for those diseases caused by *Streptococcus*; and antifungal treatment, preferably for those diseases caused by *Candida*.

On the other hand, the use of a compound of formula I is claimed in the manufacture of a medicament. In a particular embodiment, the compound of formula I is used in the manufacture of a medicament for cancer, preferably breast, lung, colorectal or pancreatic cancer. In another particular embodiment, the compound of formula I is used in the manufacture of a medicament for the treatment of viral diseases, preferably those caused by Adenovirus; as well as in the manufacture of a medicament for antiparasitic treatment, preferably for those diseases caused by *Plasmodium* or *Trypanosoma*; in the manufacture of a medicament for the treatment of bacterial disease, preferably those caused by *Streptococcus*, and in the manufacture of a drug for the treatment of fungal diseases, preferably those caused by *Candida*.

In its third object, the invention provides pharmaceutical formulations comprising at least one compound of formula I as an active ingredient. Said pharmaceutical formulations can contain one or more excipients and/or carrier substances. Furthermore, said formulations can contain any other active ingredient inhibiting the function of the choline kinase enzyme.

The excipients, carrier substances and auxiliary substances must be pharmaceutically and pharmacologically tolerable, such that they can be combined with other components of the formulation or preparation and do not have adverse effects in the organism treated. The pharmaceutical compositions or formulations include those that are suitable for oral or parenteral administration (including subcutaneous, intradermal, intramuscular and intravenous administration), although the best administration route depends on the conditions of the patient. The formulations can be in the form of single doses the formulations can be prepared according to methods known in the field of pharmacology. The amounts of active substances to be administered can vary according to the particularities of the therapy.

The invention also provides a method for preparing the compounds of formula I. This object of the invention has two different embodiments according to whether the compound of formula I has the same or different aminopyridinium groups.

a) Process for obtaining the compounds of formula I in which the aminopyridinium groups are the same: The process comprises reacting the corresponding heterocyclic derivative of formula VII and the dihalogenated derivative $AX_2$ (where X represents the halogen atom: Cl, Br or I) in 2:1 molar amounts in an organic solvent. The reaction preferably takes place in butanone, in a closed tube and at a temperature of 90 to 110° C.

b) Process for obtaining the compounds of formula I in which the aminopyridinium groups are different: The process comprises reacting the corresponding heterocyclic derivative of formula VII and the dihalogenated derivative $AX_2$ (where X represents the halogen atom: Cl, Br or I) in 1:1 molar amounts in an organic solvent, in order to give a monoquaternized product which is again reacted with another different heterocyclic derivative molecule, in a 1:1 molar ratio, using another organic solvent that is more polar than the first one so that the previously formed monoquaternized salt can be dissolved. The first step of the reaction preferably takes place in butanone, in a closed tube and at a temperature of 90 to 110° C.; whereas the second step is preferably carried out in ethanol in a closed tube and at a temperature of 90 to 110° C.

Finally, in its last object, the invention provides the compounds of formula VII participating as starting compounds in the method for preparing the compounds of formula I.

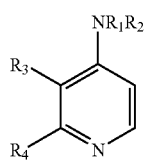

VII where $R_1$ represents a radical selected from the group formed by H and $C_{1-6}$ alkyl optionally substituted by trifluoromethyl, hydroxyl or alkoxyl;

$R_2$ represents an aryl radical optionally substituted by halogen, trifluoromethyl, hydroxyl, $C_{1-6}$ alkyl, amino or alkoxyl;

$R_3$ represents either a radical selected from the group formed by H, halogen, trifluoromethyl, hydroxyl, amino, alkoxyl and $C_{1-6}$ alkyl optionally substituted by trifluoromethyl, hydroxyl, amino or alkoxyl, or together with $R_4$ a —CH=CH—CH=CH— radical optionally substituted by halogen, trifluoromethyl, hydroxyl, $C_{1-6}$ alkyl, amino or alkoxyl;

$R_4$ represents either a radical selected from the group formed by H, and $C_{1-6}$ alkyl optionally substituted by halogen, trifluoromethyl, hydroxyl, amino or alkoxyl, or together with $R_3$ a —CH=CH—CH=CH— radical optionally substituted by halogen, trifluoromethyl, hydroxyl, $C_{1-6}$ alkyl, amino or alkoxyl.

Among the compounds preferred among the compounds of formula VII are the compounds of formula VIII:

VIII

| Compound | $R^1$ | $R^2$ | R |
|---|---|---|---|
| A | Me | —⟨benzene⟩—Cl | H |
| B | Me | —⟨benzene⟩—Cl | Cl |

The following examples are set forth as an illustration of the present invention:

EXAMPLES

Preparation Examples

Compound 1 (Code ACG560B): 1,1'-(benzene-1,3-diylmethylene)bis[4-(4-chloro-N-methylanilino)pyridinium]dibromide The mixture of 4-(4-chloro-N-methylaniline)pyridine (125 mg, 0.57 mmol) and 1,3-bis(bromomethyl)benzene (75 mg, 0.28 mmol) in dry butanone (40 ml) was heated in a closed tube at 100° C. for 144 hours. After filtration and rigorous washing with butanone, EtOAc and $Et_2O$, compound 1 was obtained pure as a white solid (125.2 mg, 62.7%); m.p.: 197-198° C. $^1$H NMR (400 MHz, DMSO-$d_6$), δ 8.48 (d, 4H, H-2,$6_{pyr}$, J=6.6); 7.64 (d, 4H, H-3,$5_{anil}$, J=8.6); 7.57 (s, 1H, H-$2_{Ph}$); 7.45 (d, 5H, H-2,$6_{anil}$ and H-$5_{Ph}$; J=8.6); 7.37 (d, 2H, H-4,$6_{Ph}$, J=7.7); 6.95 (bs, 4H, H-3,$5_{pyr}$); 5.49 (s, 4H, $CH_2N^+$); 3.46 (s, 6H, Me). $^{13}$C-NMR (100 MHz, DMSO-$d_6$), δ 156.20 (C-$4_{pyr}$); 142.75 (C-2,$6_{pyr}$); 141.96 (C-$1_{anil}$); 136.18 (C-$1.3_{Ph}$); 132.78 (C-$4_{anil}$); 130.50 (C-3,$5_{anil}$); 129.73 (C-$5_{Ph}$); 128.37 (C-2,$6_{anil}$); 128.18 (C-4,$6_{Ph}$); 127.89 (C-$2_{Ph}$); 109.15 (C-3,$5_{pyr}$); 59.16 ($CH_2N^+$); 41.42 (Me). HRMS (m/z): Calculated for $C_{32}H_{30}N_4Cl_2Br$ (M-Br)$^+$ 619.1031; found: 619.1031. Analysis for $C_{32}H_{30}N_4Cl_2Br_2 \cdot 1H_2O$. Calculated: C, 53.43; H, 4.56; N, 7.63%. Found: C, 53.14; H, 4.48; N, 7.79%.

Compound 2 (Code ACG416B): 1,1'-(biphenyl-3,3'-diylmethylene)bis[4-(N-methylanilino)pyridinium] dibromide The mixture of 4-(N-methylaniline)pyridine (216 mg, 1.17 mmol) and 3,3'-bis(bromomethyl)biphenyl (200 mg, 0.58 mmol) in dry butanone (40 ml) was heated in a closed tube at a 100° C. for 24 hours. After filtration and thorough washing with butanone, the solid product was purified by recrystallization from MeOH and the residue was ground with $Et_2O$. Compound 2 was obtained as a white solid (294 mg, 71.5%); m.p.: 124-125° C. $^1$H-NMR (300 MHz, $CD_3OD$), δ 8.35 (bs, 4H, H-$2,6_{pyr}$); 7.84 (s, 2H, H-$2_{Ph}$); 7.67 (d, 2H, H-$6_{Ph}$, J=7.7); 7.56 (t, 4H, H-$3,5_{anil}$, J=7.6); 7.50-7.44 (m, 4H, H-$5_{Ph}$ and H-$4_{nil}$); 7.39 (d, 2H, H-$4_{Ph}$, J=7.7); 7.33 (d, 4H, H-$2,6_{anil}$, J=7.5); 6.95 (bs, 4H, H-$3,5_{pyr}$); 5.47 (s, 4H, $CH_2N^+$); 3.51 (s, 6H, Me). $^{13}$C-NMR (75 MHz, $CD_3OD$), δ 158.48 (C-$4_{pyr}$); 144.82 (C-$1_{anil}$); 143.80 (C-$2,6_{pyr}$); 142.60 (C-$1_{Ph}$); 136.82 (C-$3_{Ph}$); 132.01 (C-$3,5_{anil}$); 131.14 (C-$5_{Ph}$); 130.12 (C-$4_{anil}$); 128.99 (C-$4_{Ph}$); 128.82 (C-$6_{Ph}$); 128.58 (C-$2_{Ph}$); 127.52 (C-$2,6_{anil}$) 110.29 (C-$3,5_{pyr}$); 61.97 ($CH_2N^+$); 41.42 (Me). HRMS (m/z): Calculated for $C_{38}H_{36}N_4Br$ $(M-Br)^+$ 627.2123; found: 627.2122. Analysis for $C_{38}H_{36}N_4Br_2.2.5H_2O$. Calculated: C, 60.56; H, 5.48; N, 7.43%. Found: C, 60.70; H, 5.83; N, 7.20%.

Compound 3 (Code ACG548B): 1,1'-(biphenyl-3,3'-diylmethylene)bis[4-(4-chloro-N-methylanilino)pyridinium]dibromide The mixture of 4-(4-chloro-N-methylanilino)pyridine (235 mg, 1.07 mmol) and 3,3'-bis(bromomethyl)biphenyl (183 mg, 0.53 mmol) in dry butanone (40 ml) was heated in a closed tube at 100° C. for 24 hours. After filtration and thorough washing with $CHCl_3$, the solid product was purified by recrystallization from MeOH, after adding $Et_2O$ until turbidity. Compound 3 was obtained as a white solid (205 mg, 49.7%); m.p.: 279-280° C. $^1$H-NMR (300 MHz, DMSO-$d_6$), δ 8.57 (d, 4H, H-$2,6_{pyr}$, J=6.5); 7.88 (s, 2H, H-$2_{Ph}$); 7.67 (d, 2H, H-$6_{Ph}$, J=7.7); 7.61 (d, 4H, H-$3,5_{anil}$, J=8.6); 7.51 (t, 2H, H-$5_{Ph}$, J=7.7); 7.42 (d, 6H, H-$4_{Ph}$ and H-$2,6_{anil}$, J=8.6); 6.99 (bs, 4H, H-$3,5_{pyr}$); 5.51 (s, 4H, $CH_2N^+$); 3.43 (s, 6H, Me). $^{13}$C-NMR (75 MHz, DMSO-$d_6$), δ 156.20 (C-$4_{pyr}$); 142.72 (C-$2,6_{pyr}$); 142.05 (C-$1_{anil}$); 140.01 (C-$1_{Ph}$); 136.20 (C-$3_{Ph}$); 132.79 (C-$4_{anil}$); 130.53 (C-$3,5_{anil}$); 129.73 (C-$5_{Ph}$); 128.47 (C-$2,6_{anil}$); 127.51 (C-$4_{Ph}$); 127.14 (C-$6_{Ph}$); 127.04 (C-$2_{Ph}$); 109.20 (C-$3,5_{pyr}$); 59.55 ($CH_2N^+$); 40.73 (Me). HRMS (m/z): Calculated for $C_{38}H_{34}N_4Cl_2Br$ $(M-Br)^+$ 695.1344; found: 695.1344. Analysis for $C_{38}H_{34}N_4Cl_2Br_2.1.2H_2O$. Calculated: C, 57.12; H, 4.59; N, 7.01%. Found: C, 57.55; H, 4.99; N, 6.97%.

Compound 4 (Code ACG604A): 1,1'-(biphenyl-3,3'-diylmethylene)bis[4-(3,5-dichloro-N-methylanilino)pyridinium]dibromide The mixture of 4-(3,5-dichloro-N-methylaniline)pyridine (200 mg, 0.80 mmol) and 3,3'-bis(bromomethyl)biphenyl (136 mg, 0.40 mmol) in dry butanone (40 ml) was heated in a closed tube at 100° C. for 72 hours. After filtration and thorough washing with butanone $Et_2O$, compound 4 was obtained as a pure white solid (270 mg, 79.7%); m.p.: 312-313° C. $^1$H-NMR (300 MHz, DMSO-$d_6$), δ 8.63 (d, 4H, H-$2,6_{pyr}$, J=7.1); 7.92 (s, 2H, H-$2_{Ph}$); 7.75 (s, 2H, H-$4_{nil}$); 7.70 (d, 2H, H-$6_{Ph}$, J=7.6); 7.62 (d, 4H, H-$2,6_{anil}$, J=1.8); 7.53 (t, 2H, H-$5_{Ph}$, J=7.6); 7.45 (d, 2H, H-$4_{Ph}$, J=7.6); 7.04 (d, 4H, H-$3,5_{pyr}$, J=7.1); 5.56 (s, 4H, $CH_2N^+$); 3.44 (s, 6H, Me). $^{13}$C-NMR (75 MHz, DMSO-$d_6$), δ 156.20 (C-$4_{pyr}$); 145.27 (C-$1_{anil}$); 142.86 (C-$2,6_{pyr}$); 140.08 (C-$1_{Ph}$); 136.11 (C-$3_{Ph}$); 135.34 (C-$3,5_{anil}$); 129.70 (C-$5_{Ph}$); 128.33 (C-$4_{anil}$); 127.55 (C-$4_{Ph}$); 127.14 (C-$6_{Ph}$); 127.07 (C-$2_{Ph}$); 125.97 (C-$2,6_{anil}$); 109.53 (C-$3,5_{pyr}$); 59.65 ($CH_2N^+$); 40.59 (Me). HRMS (m/z); Calculated for $C_{38}H_{32}N_4Cl_4Br$ $(M-Br)^+$ 763.0564; found: 763.0563. Analysis for $C_{38}H_{32}N_4Cl_4Br_2.0.1H_2O$. Calculated: C, 53.81; H, 3.81; N, 6.60%. Found: C, 53.41; H, 4.19; N, 6.25%.

Compound 5 (Code RSM964A): 1,1'-(biphenyl-3,3'-diylmethylene)bis[4-(4-chloro-N-methylanilino)quinolinium]dibromide The mixture of 4-(4-chloro-N-methylanilino)quinoline (212 mg, 0.78 mmol) and 3,3'-bis(bromomethyl)benzene (134 mg, 0.39 mmol) in dry butanone (40 ml) was heated in a closed tube at 100° C. for 72 hours. After filtration and thorough washing with butanone, EtOAc and $Et_2O$, compound 5 was obtained as a pure yellowish solid (134 mg, 40%); m.p.: 217-218° C. $^1$H-NMR (300 MHz, DMSO-$d_6$): δ 9.24 (d, J=7.4, 2H, H-$2_{quin}$); 8.18 (d, J=8.9, 2H, H-$8_{quin}$); 7.84 (s, 2H, H-$2_{Ph}$); 7.63 (d, J=7.5, 2H, H-$5_{quin}$); 7.56-7.43 (m, 18H, H-$5,6ph$, H-$2,3,5,6_{anil}$ H-$3,6,7_{quin}$); 7.23 (d, J=7.4, 2H, H-$4_{Ph}$); 6.08 (s, 4H, $N^+$—$CH_2$); 3.74 (s, 6H, Me). $^{13}$C-NMR (100 MHz, DMSO-$d_6$): δ 157.87 (C-$4_{quin}$); 147.46 (C-$2_{quin}$); 146.42 (C-$1_{anil}$); 140.03 (C-$1_{Ph}$); 138.83 (C-$8a_{quin}$); 135.61 (C-$3_{Ph}$); 133.50 (C-$7_{quin}$); 131.69 (C-$4_{anil}$); 130.27 (C-$3,5_{anil}$); 129.62 (C-$5_{Ph}$); 127.35 (C-$6_{Ph}$); 127.18 (C-$2,6_{anil}$); 126.73 (C-$6_{quin}$); 126.09 (C-$4_{Ph}$); 125.87 (C-$5_{quin}$); 125.67 (C-$2_{Ph}$); 119.65 (C-$4a_{quin}$); 119.14 (C-$8_{quin}$); 107.10 (C-$3_{quin}$); 57.28 ($N^+$—$CH_2$); 44.94 (Me). HRMS (m/z): Calculated for $C_{46}H_{38}N_4Cl_2Br_2$ $[(M-Br)]^+$ 795.1657. Found: 795.1656. Analysis for $C_{46}H_{38}N_4Cl_2Br_2.3H_2O$. Calculated: C, 59.31; H, 4.76; N, 6.01%. Found: C, 59.24; H, 4.70; N, 5.65%.

Compound 6 (Code RSM820C): 1,1'-(biphenyl-3,3'-diylmethylene)bis[4-(4-chloro-N-methylanilino)-7-chloroquinolinium]dibromide The mixture of 7-chloro-4-(4-chloro-N-methylanilino)quinoline (300 mg, 0.98 mmol) and 3,3'-bis(bromomethyl)biphenyl (168 mg, 0.49 mmol) in dry butanone (40 ml) was heated in a closed tube at 100° C. for 72 hours. After filtration and thorough washing with butanone and $CHCl_3$, the solid product was purified by recrystallization from EtOH or EtOH/MeOH, after adding $Et_2O$ until turbidity. Compound 6 was obtained as a yellowish solid (154 mg, 45%); m.p.: 220-221° C. $^1$H-NMR (300 MHz, DMSO-$d_6$): δ 9.19 (d, J=7.5, 2H, H-$2_{quin}$); 8.29 (d, J=1.7, 2H, H-$8_{quin}$); 7.85 (s, 2H, H-$2_{Ph}$); 7.64 (d, J=7.2, 2H, H-$5_{quin}$); 7.57-7.45 (m, 16H, H-$5,6_{Ph}$, H-$2,3,5,6_{anil}$, H-$3,6_{quin}$); 7.25 (d, J=7.7, 2H, H-$4_{Ph}$); 6.08 (s, 4H, $N^+$—$CH_2$); 3.73 (s, 6H, Me). $^{13}$C-NMR (75 MHz, DMSO-$d_6$): δ 157.68 (C-$4_{quin}$); 148.01 (C-$2_{quin}$); 146.14 (C-$1_{anil}$); 140.14 (C-$1_{Ph}$); 139.85 (C-$8a_{quin}$); 138.48 (C-$7_{quin}$); 135.51 (C-$3_{Ph}$); 132.11 (C-$4_{anil}$); 130.50 (C-$3,5_{anil}$); 129.80 (C-$5_{Ph}$); 129.45 (C-$6_{Ph}$); 127.32 (C-$2,6_{anil}$); 126.89 (C-$6_{quin}$); 126.12 (C-$4_{Ph}$); 125.91 (C-$5_{quin}$); 125.82 (C-$2_{Ph}$); 118.48 (C-$8_{quin}$); 118.35 (C-$4_{quin}$); 107.38 (C-$3_{quin}$); 57.14 ($N^+$—$CH_2$); 45.18 (Me). HRMS (m/z): Calculated for $C_{46}H_{36}N_4Cl_4Br_2$ $[(M-HBr-Br)]^+$ 783.1616. Found: 783.1616. Analysis for $C_{46}H_{36}N_4Cl_4Br_2.1.5H_2O$. Calculated: C, 56.76; H, 4.04; N, 5.76%. Found: C, 56.72; H, 4.18; N, 5.71%.

Compound 7 (Code RSM932A): 1,1'-(biphenyl-4,4'-diylmethylene)bis[4-(4-chloro-N-methylanilino)quinolinium]dibromide The mixture of 4-(4-chloro-N-methylaniline) quinoline (240 mg, 0.89 mmol) and 4,4'-bis(bromomethyl)biphenyl (152 mg, 0.44 mmol) in dry butanone (40 ml) was heated in a closed tube at 100° C. for 72 hours. After filtration and thorough washing with butanone, compound 7 was obtained as a pure yellowish solid (121 mg, 30%); m.p.: 255-257° C. $^1$H-NMR (300 MHz, DMSO-d$_6$): δ 9.19 (d, J=7.4, 2H, H-2$_{quin}$); 8.12 (d, J=8.9, 2H, H-8$_{quin}$); 7.83 (pst, J=7.5, 2H, H-7$_{quin}$); 7.66 (d, J=8.2, 2H, H-5$_{quin}$); 7.55 (d, J=8.8, 4H, H-3,5$_{anil}$); 7.44 (d, J=8.9, 4H, H-2,6$_{anil}$); 7.56-7.39 (m, 12H, H-2,3,5,6$_{Ph}$, H-3$_{quin}$, H-6$_{quin}$); 6.05 (s, 4H, N$^+$—CH$_2$); 3.73 (s, 6H, Me). $^{13}$C-NMR (75 MHz, DMSO-d$_6$): δ157.86 (C-4$_{quin}$); 147.41 (C-2$_{quin}$); 146.40 (C-1$_{anil}$); 139.11 (C-1$_{Ph}$); 138.78 (C-8a$_{quin}$); 134.30 (C-4$_{Ph}$); 133.47 (C-7$_{quin}$); 131.69 (C-4$_{anil}$); 130.26 (C-3,5$_{anil}$); 127.34 (C-3,5$_{Ph}$); 127.18 (C-2,6$_{quin}$), (C-2,6$_{Ph}$); 127.08 (C-6$_{quin}$); 126.08 (C-5$_{quin}$); 119.65 (C-4a$_{quin}$); 119.12 (C-8$_{quin}$); 107.06 (C-3$_{quin}$); 56.94 (N$^+$—CH$_2$); 44.94 (Me). HRMS (m/z): Calculated for C$_{46}$H$_{38}$N$_4$Cl$_2$Br$_2$ [(M-Br)]$^+$ 795.1657. Found: 795.1658. Analysis for C$_{46}$H$_{38}$N$_4$Cl$_2$Br$_2$.2H$_2$O. Calculated: C, 60.48; H, 4.63; N, 6.13%. Found: C, 60.06; H, 4.48; N, 5.87%.

Compound 8 (Code RSM824B): 1,1'-(biphenyl-4,4'-diylmethylene)bis[4-(4-chloro-N-methylanilino)-7-chloroquinolinium]dibromide The mixture of 7-chloro-4-(4-chloro-N-methylanilino)quinoline (300 mg, 0.98 mmol) and 4,4'-bis(bromomethyl)biphenyl (168 mg, 0.49 mmol) in dry butanone (100 ml) was heated in a closed tube at 100° C. for 72 hours. After filtration and thorough washing with butanone, compound 8 was obtained as a pure yellowish solid (195 mg, 48%); m.p.: 276-277° C. $^1$H-NMR (400 MHz, DMSO-d$_6$): δ 9.14 (d, J=7.4, 2H, H-2$_{quin}$); 8.23 (d, J=1.6, 2H, H-8$_{quin}$); 7.73 (d, J=8.3, 2H, H-5$_{quin}$); 7.69 (d, J=8.4, 4H, H-2,6$_{Ph}$); 7.56 (d, J=8.8, 4H, H-3,5$_{anil}$); 7.46 (d, J=8.9, 4H, H-2,6$_{anil}$); 7.50-7.46 (m, 6H, H-6$_{quin}$ H-3$_{quin}$); 7.41 (d, J=8.4, 4H, H-3,5$_{Ph}$); 6.04 (s, 4H, N$^+$—CH$_2$); 3.73 (s, 6H, Me). $^{13}$C-NMR (100 MHz, DMSO-d$_6$): δ 157.69 (C-4$_{quin}$); 147.98 (C-2$_{quin}$); 146.13 (C-1$_{anil}$); 139.82 (C-8a$_{quin}$); 139.21 (C-1$_{Ph}$); 138.51 (C-7$_{quin}$); 134.22 (C-4$_{Ph}$); 132.14 (C-4$_{anil}$); 130.50 (C-3,5$_{anil}$); 129.45 (C-2,6$_{anil}$); 127.54 (C-3,5$_{Ph}$); 127.33 (C-6$_{quin}$); 127.23 (C-2,6$_{Ph}$); 126.52 (C-5$_{quin}$); 118.47 (C-8$_{quin}$); 118.35 (C-4a$_{quin}$); 107.33 (C-3$_{quin}$); 56.83 (N$^+$—CH$_2$); 45.19 (Me). HRMS (m/e): Calculated for C$_{46}$H$_{36}$N$_4$Cl$_4$Br$_2$ [(M–HBr—Br)]$^+$ 783.1616. Found: 783.1614. Analysis for C$_{46}$H$_{36}$N$_4$Cl$_4$Br$_2$. Calculated: C, 58.38; H, 3.83; N, 5.92%. Found: C, 58.73; H, 3.96; N, 5.74%.

Compound 9 (Code RSM936A): 1,1'-[ethylenebis(benzene-1,4-diylmethylene)]bis[4-(4-chloro-N-methylanilino)quinolinium]dibromide The mixture of 4-(4-chloro-N-methylanilino)quinoline (204 mg, 0.76 mmol) and 4,4'-bis(bromomethyl)bibenzyl (140 mg, 0.37 mmol) in dry butanone (40 ml) was heated in a closed tube at 100° C. for 72 hours. After filtration and thorough washing with butanone and CHCl$_3$, compound 9 was obtained as a pure yellowish solid (70 mg, 20%); m.p.: 212-214° C. $^1$H-NMR (300 MHz, DMSO-d$_6$): δ 9.19 (d, J=7.4, 2H, H-2$_{quin}$); 8.10 (d, J=8.9, 2H, H-8$_{quin}$); 7.82 (pst, J=7.5, 2H, H-7$_{quin}$); 7.54 (d, J=8.8, 4H, H-3,5$_{anil}$); 7.44 (d, J=8.9, 4H, H-2,6$_{anil}$); 7.52-7.39 (m, 6H, H-3$_{quin}$, H-5$_{quin}$, H-6$_{quin}$); 7.24 (s, 8H, H-2,3,5,6$_{Ph}$); 5.98 (s, 4H, N$^+$—CH$_2$); 3.73 (s, 6H, Me); 2.80 (s, 4H, CH$_2$-Ph). $^{13}$C-NMR (100 MHz, DMSO-d$_6$): δ 157.80 (C-4$_{quin}$); 147.34 (C-2$_{quin}$); 146.44 (C-1$_{quin}$); 141.55 (C-1$_{Ph}$); 138.74 (C-8a$_{quin}$); 133.36 (C-7$_{quin}$); 132.32 (C-4$_{Ph}$); 131.63 (C-4$_{anil}$); 130.25 (C-3,5$_{anil}$); 128.79 (C-3,5$_{Ph}$); 127.26 (C-6$_{quin}$); 127.17 (C-2,6$_{anil}$); 126.74 (C-2,6$_{Ph}$); 126.04 (C-5$_{quin}$); 119.66 (C-4a$_{quin}$); 119.19 (C-8$_{quin}$); 107.06 (C-3$_{quin}$); 57.10 (N$^+$—CH$_2$); 44.93 (Me); 36.22 (CH$_2$-Ph). HRMS (m/z): Calculated for C$_{48}$H$_{42}$N$_4$Cl$_2$Br$_2$ [(M-Br)]$^+$ 823.1970. Found: 823.1970. Analysis for C$_{48}$H$_{42}$N$_4$Cl$_2$Br$_2$.1H$_2$O. Calculated: C, 62.42; H, 4.80; N, 6.07%. Found: C, 62.29; H, 4.59; N, 6.09%.

Compound 10 (Code RSM828B): 1,1'-[ethylenebis(benzene-1,4-diylmethylene)]bis[4-(4-chloro-N-methylanilino)-7-chloroquinolinium]dibromide The mixture of 7-chloro-4-(4-chloro-N-methylanilino)quinoline (300 mg, 0.98 mmol) and 4,4'-bis(bromomethyl)bibenzyl (182 mg, 0.49 mmol) in dry butanone (40 ml) was heated in a closed tube at 100° C. for 72 hours. After filtration and thorough washing with butanone, compound 10 was obtained as a pure yellowish solid (229 mg, 48%); m.p.: 256-257° C. $^1$H-NMR (400 MHz, DMSO-d$_6$): δ 9.11 (d, J=7.4, 2H, H-2$_{quin}$); 8.18 (d, J=1.5, 2H, H-8$_{quin}$); 7.55 (d, J=8.8, 4H, H-3,5$_{anil}$); 7.46 (d, J=8.8, 4H, H-2,6$_{anil}$); 7.56-7.44 (m, 6H, H-3$_{quin}$, H-5$_{quin}$, H-6$_{quin}$); 7.24 (s, 8H, H-2,3,5,6$_{Ph}$); 5.97 (s, 4H, N$^+$—CH$_2$); 3.72 (s, 6H, Me); 2.82 (s, 4H, CH$_2$-Ph). $^{13}$C-NMR (100 MHz, DMSO-d$_6$): δ 157.63 (C-4$_{quin}$); 147.91 (C-2$_{quin}$); 146.16 (C-1$_{anil}$); 141.74, 139.75 and 138.88 (C-7$_{quin}$, C-8a$_{quin}$ and C-4$_{Ph}$); 132.20 (C-4$_{anil}$); 132.08 (C-1$_{Ph}$); 130.50 (C-3,5$_{anil}$); 129.39 (C-6$_{quin}$); 128.99 (C-3,5$_{Ph}$); 127.32 (C-2,6$_{anil}$); 126.90 (C-2,6$_{Ph}$); 126.48 (C-5$_{quin}$); 118.55 (C-8$_{quin}$); 118.35 (C-4a$_{quin}$); 107.32 (C-3$_{quin}$); 57.02 (N$^+$—CH$_2$); 45.17 (Me); 36.33 (CH$_2$-Ph). HRMS (m/z): Calculated for C$_{48}$H$_{40}$N$_4$Cl$_4$Br$_2$ [(M–HBr—Br)]$^+$ 811.1927. Found: 811.1926. Analysis for C$_{48}$H$_{40}$N$_4$Cl$_4$Br$_2$.2H$_2$O. Calculated: C, 57.05; H, 4.39; N, 5.54%. Found: C, 57.14; H, 4.07; N, 5.46%.

Reagent Preparation

The compound α,α'-dibromo-m-xylene is a commercial product supplied by Sigma-Aldrich Química S. A. with address at Avenida Valdelaparra No. 51-53, 28100 Alcobendas (Madrid).

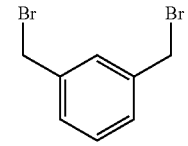

α, α'-dibromo-m-xylene

The following starting materials were prepared by means of the methods described in the respective references 1.—3,3'-bis(bromomethyl)biphenyl

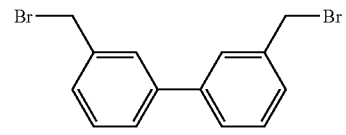

Werner, W. *J. Org. Chem.* 17, 523-528 (1952)

2.—4,4'-bis(bromomethyl)biphenyl

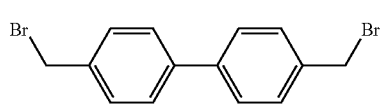

Szendey, G. L., Munnes, S. *Chem. Ber.* 94, 38-42 (1961); Staab, H. A., Haenel, M. *Chem. Ber.* 106, 2190-2202 (1973)

3.—Bis-p-(bromomethyl)bibenzyl

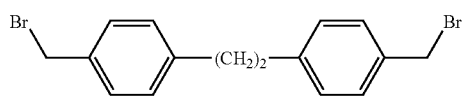

Cram, D. J., Steinberg, J. *J. Am. Chem. Soc.* 73, 5691-5704 (1951)

4.—4-(N-Methylanilino)pyridine

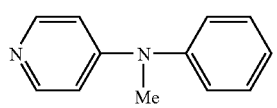

Campos, J., Núñez, M. C., Sánchez, R., Gómez-Vidal, J. A., Rodríguez-González, A., Báñez, M., Gallo, M. Á., Lacal, J. C., Espinosa, A. *Bioorg. & Med. Chem.* 10, 2215-2231 (2002)

5.—4-(4-Chloro-N-methylanilino)pyridine

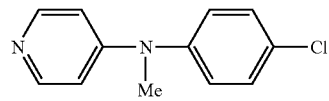

Conejo-García, A., Campos, J., Sánchez, R., Rodríguez-González, A., Lacal, J. C., Gallo, M. Á., Espinosa, A. *Eur. J. Med. Chem.* 38, 109-116 (2003).

6.—4-(3,5-dichloro-N-methylanilino)pyridine

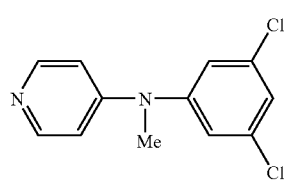

This compound was prepared from 4-chloropyridine hydrochloride and 4-(3,5-dichloro-N-methylanilino)pyridine according to the process described previously in: Conejo-García, A., Campos, J., Sánchez, R., Rodríguez-González, A., Lacal, J. C., Gallo, M. Á., Espinosa, A. *Eur. J. Med. Chem.* 38, 109-116 (2003). On the other hand, 3,5-dichloro-N-methylanilino was obtained by following the process described in the following work: Leeson, P. D., Baker, R., Carling, R. W., Curtis, N. R., Moore, K. W., Williams, B. J., Foster, A. C., Donald, A. E., Kemp, J. A., Marshall, G. R. *J. Med. Chem.* 34, 1243-1252 (1991).

7.—4,4'-Bis(chloromethyl)-[2,2']bithiazolyl.

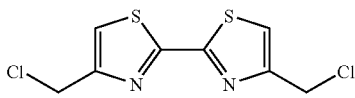

Ref.: Chi, AND. F.; Chu, T. I. *Record (Peking)*, 1, 45 (1957); *Chem. Abstract,* 52, 6321 a,b (1957).

8.—Diethyl 4,4'-Bis(bromomethyl)-[2,2']bithiazolyl-5,5'-dicarboxylate

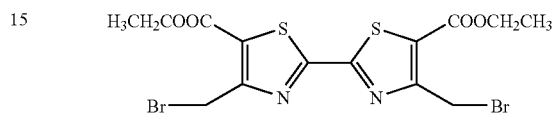

Ref.: Lehn, J.-M.; Regnouf de Vains, J.-B. *Tetrahedron Lett.,* 30, 2209-2212 (1989).

9.—6,6'-Bis(bromomethyl)-[2,2']bipyridine

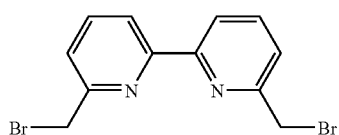

Ref.: Rodríguez-Ubis, J.-C.; Alpha, B.; Plancherel, D.; Lehn, J.-M. *Helv. Chim. Acta,* 67, 2264 (1984).

10.—6,6'-Bis(bromomethyl)-4,4'-dimethyl-[2,2']bipyrimidinyl

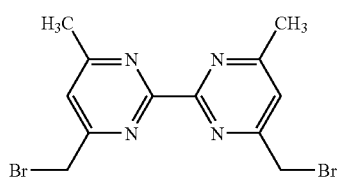

Ref.: Lehn, J.-M.; Regnouf de Vains, J.-B. *Tetrahedron Lett.,* 30, 2209-2212 (1989).

Preparation PF New Starting Materials

The compounds of formula VII:

$$\underset{\text{VII}}{\text{R}_3\text{-}\underset{\text{R}_4}{\overset{\text{NR}_1\text{R}_2}{\text{pyridine}}}}$$

can be prepared by reacting the 4-aniline or quinoline derivative with the corresponding 4-chloro-aniline in glacial acetic acid with reflux. After cooling, the solution is basified with sodium hydroxide solution and the resulting suspension is subsequently concentrated and purified by flash chromatography.

Examples of obtaining the compounds of formula VIII

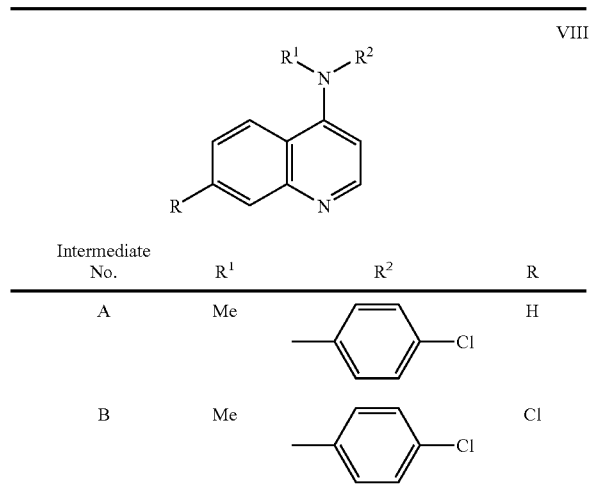

| Intermediate No. | $R^1$ | $R^2$ | R |
|---|---|---|---|
| A | Me | 4-Cl-C6H4 | H |
| B | Me | 4-Cl-C6H4 | Cl | are provided below:

Compound VIII A 4-(4-chloro-N-methylanilino)quinoline

A solution of 4-chloroquinoline (5 mmol) and of 4-chloro-N-methylaniline (10 mmol) in glacial acetic acid (15 ml) was heated with reflux for 3 h under a stream of argon. After cooling, the solution was basified with a 10% NaOH solution until pH=10 and the resulting suspension was concentrated in a rotary evaporator and purified by means of flash chromatography (9:1, $CH_2Cl_2$:MeOH) to give the target molecule as a yellowish syrup (97%). $^1$H-NMR (400 MHz, $CDCl_3$): δ 8.10 (d, J=8.5, 1H, H-$2_{quin}$); 7.70 (d, J=8.5, 1H, H-$5_{quin}$); 7.65 (t, J=7.9, 1H, H-$7_{quin}$); 7.38 (t, J=8.5, 1H, H-$6_{quin}$); 7.35 (d, J=7.9, 1H, H-$8_{quin}$); 7.17 (d, J=8.9, 2H, H-$3,5_{anil}$); 7.14 (d, J=8.5, 1H, H-$3_{quin}$); 6.76 (d, J=8.9, 2H, H-$2,6_{anil}$); 3.45 (s, 6H, Me). $^{13}$C-NMR (100 MHz, $CDCl_3$): δ 153.37 (C-$4_{quin}$); 151.16 (C-$2_{quin}$); 150.01 (C-$1_{anil}$); 148.17 (C-$8a_{quin}$); 135.02 (C-$4_{anil}$); 130.07 (C-$7_{quin}$); 129.52 (C-$6_{quin}$); 129.29 (C-3,$5_{anil}$); 126.26 (C-$4a_{quin}$); 126.07 (C-$5_{quin}$); 124.40 (C-$8_{quin}$); 119.79 (C-$2,6_{anil}$); 115.08 (C-$3_{quin}$); 41.75 (Me). HRMS (m/z): Calculated for $C_{16}H_{13}N_2Cl$ [(M+H)]$^+$ 269.0845. Found: 269.0845. Analysis for $C_{16}H_{13}N_2Cl$. Calculated: C, 71.51; H, 4.88; N, 10.42%. Found: C, 71.60; H, 4.71; N, 10.33%.

Compound VIII B 7-chloro-4-(4-chloro-N-methylanilino)quinoline

A solution of 4,7-dichloroquinoline (5 mmol) and of 4-chloro-N-methylaniline (10 mmol) in glacial acetic acid (15 ml) was heated with reflux for 3 h under a stream of argon. After cooling, the solution was basified with a 10% NaOH solution until pH=10 and the resulting suspension was concentrated in a rotary evaporator and purified by means of flash chromatography (9:1, $CH_2Cl_2$:MeOH) to give the intermediate II as a yellowish syrup (59%) $^1$H-NMR (300 MHz, $CH_3OD$): δ 8.66 (d, J=7.1, 1H, H-$2_{quin}$); 7.94 (d, J=2.0, 1H, H-$8_{quin}$); 7.53 (d, J=8.8, 2H, H-$3,5_{anil}$); 7.41-7.37 (m, 2H, H-$5,6_{quin}$); 7.47 (d, J=8.8, 2H, H-$2,6_{anil}$); 7.32 (d, J=7.1, 2H, H-$3_{quin}$); 3.76 (s, 3H, Me). $^{13}$C-NMR (75 MHz, $CH_3OD$): δ 159.86 (C-$4_{quin}$); 147.63 (C-$7_{quin}$); 143.86 (C-$2_{quin}$); 141.46 (C-$1_{anil}$); 140.56 (C-$8a_{quin}$); 135.02 (C-$4_{anil}$); 132.01 (C-3,$5_{anil}$); 129.92 (C-$6_{quin}$); 128.58 (C-$2,6_{anil}$); 127.98 (C-$5_{quin}$); 120.56 (C-$8_{quin}$); 118.71 (C-$4a_{anil}$); 107.38 (C-$3_{quin}$); 45.74 (Me). HRMS (m/z): Calculated for $C_{16}H_{12}N_2Cl_2$ [(M+H)]$^+$ 303.0456. Found: 303.0456. Analysis for $C_{16}H_{12}N_2Cl_2$. Calculated: C, 63.38; H, 3.99; N, 9.24%. Found: C, 63.46; H, 3.71; N, 9.17%.

Ex Vivo Assays of the Activity of Human Chok

Recombinant choline kinase expressed in E. coli in the buffer assay (100 mM Tris-HCl pH 8.0, 100 mM $MgCl_2$, 10 mM ATP and 200 μM of choline in the presence of methyl [$^{14}$C]-choline chloride (50-60 μCi/mmol)) was used for the ex vivo assays. The reactions were carried out at 37° C. for 30 minutes and were stopped with trichloroacetic acid cooled with ice to a final concentration of 16%. The samples were washed with diethyl ether saturated with water and were lyophilized. The hydrophilic choline derivatives were resolved in thin layer chromatography plates according to a described process [Ramírez, A., Penalva, V., Lucas, L., Lacal, J. C. Oncogene 21, 937-946 (2002)].

These assays were carried out with compounds 1-10 of the invention as well as with the compounds EC1-EC6, known compounds of the state of the art, specifically in patent ES 2 117 950. The results are summarized in table II.

Cell Proliferation Assays

The HT-29 cells were seeded in 24-well plates (35×10$^3$ cells/well) and were incubated for 24 hours. Then the cells were treated with different concentrations of ChoK inhibitors in the usual culture medium. Three days later, the wells were aspirated and both fresh medium and more amount of drug were added, and the cells were maintained for three more days. The quantification of the remaining cells in each well was carried out by means of the Crystal Violet method [Gillies, R. J., Didier, N., Denton, M. Anal. Biochem. 159, 109-113 (1986)], with some modifications [Hernández-Alcoceba, R., Saniger, L., Campos, J., Núñez, M. C., Khaless, F., Gallo, M. A., Espinosa, A., Lacal, J. C. Oncogene, 15, 2289-2301 (1997)]. Briefly, the cells were washed with TD buffer and fixed with 1% glutaraldehyde for 15 minutes. After washing again with TD, the cell nuclei were coloured with 0.1% Crystal Violet for at least 30 minutes and washed three times with distilled water. The adsorbed colouring was resuspended in 10% acetic acid and the absorbance at 595 nm was determined in a spectrometer. The results obtained are summarized in the form of an $IC_{50}$ value, i.e. the concentration of the compound required to produce 50% inhibition. This value is determined by iterative curve adjustment. Two values are determined for each point of the curve, the experiment was repeated two or three times and the mean values were estimated. In the few cases in which the two values differed more than 50%, a third experiment was carried out to determine the real value. The $IC_{50}$ value as a potency measurement is used to relate the biological activity of the compounds with their chemical structure.

These assays were carried out with compounds 1-10 of the invention as well as with compounds $EC_1$-EC6, known compounds of the state of the art, specifically in patent ES 2 117 950. The results are summarized in table II.

Toxicity Assays

Toxicity assays were carried out with 1 month old Balb C mice weighing about 25-30 grams at the start of the experiment. The mice were inoculated with different amounts of each compound in a range of 0.1 mg/kg up to 25 mg/kg, in daily doses for 5 consecutive days. After the five doses, the mice were left to rest for 9 days and both the survival and general condition were analyzed, paying special attention to the effects on their coat, behaviour, feeding habits and weight. The doses entailing a 50% mortality were recorded as the corresponding toxicity $IC_{50}$. The results obtained with the new compounds show a clear improvement of the activity when their toxicity is reduced, measured by their corresponding $IC_{50}$.

These assays were carried out with compounds 1-10 of the invention as well as with compounds EC1-EC6, known compounds of the state of the art, specifically in patent ES 2 117 950. The results are summarized in table II.

The following table II summarizes the results obtained in the assays which have been carried out.

TABLE II

| No. | Code | $R_3, R_4$* | $NR_1R_2$ | A | ex vivo $IC_{50}$ (μM) | HT-29 $IC_{50}$ (μM) | toxicity $IC_{50}$ (mg/Kg) |
|---|---|---|---|---|---|---|---|
| 1 | ACG560B | H, H | —N(Me)—C₆H₄—Cl (4-Cl) | 1,3-bis(ethyl)benzene | 5.7 | 3.3 | 17.5 |
| 2 | ACG416B | H, H | —N(Me)—C₆H₅ | 3,3'-bis(ethyl)biphenyl | 0.42 | 2.2 | 13.6 |
| 3 | ACG548B | H, H | —N(Me)—C₆H₄—Cl (4-Cl) | 3,3'-bis(ethyl)biphenyl | 1.9 | 1.9 | 20 |
| 4 | ACG604A | H, H | —N(Me)—C₆H₃—Cl₂ (3,5-diCl) | 3,3'-bis(ethyl)biphenyl | 2.6 | 1.8 | 16.7 |
| EC1 | ACG516B | H, H | pyrrolidin-1-yl | 3,3'-bis(ethyl)biphenyl | 5.8 | 2.6 | 12.5 |
| EC2 | ACG492A | H, H | piperidin-1-yl | 3,3'-bis(ethyl)biphenyl | 1.9 | 1.6 | 11.5 |
| 5 | RSM964A | —(CH=CH)₂— | —N(Me)—C₆H₄—Cl (4-Cl) | 3,3'-bis(ethyl)biphenyl | 1.3 | 1.6 | >25 |
| 6 | RSM820C | —C⁵H=C⁶H—C⁷Cl=C⁸H— | —N(Me)—C₆H₄—Cl (4-Cl) | 3,3'-bis(ethyl)biphenyl | 5.70 | 1.90 | >20 |
| EC3 | RSM856E | —C⁵H=C⁶H—C⁷Cl=C⁸H— | —NMe₂ | 3,3'-bis(ethyl)biphenyl | 9.60 | 0.70 | 2.9 |

TABLE II-continued

| No. | Code | $R_3, R_4$* | $NR_1R_2$ | A | ex vivo $IC_{50}$ (μM) | HT-29 $IC_{50}$ (μM) | toxicity $IC_{50}$ (mg/Kg) |
|---|---|---|---|---|---|---|---|
| EC4 | RSM1076A | —$C^5H$=$C^6H$— $C^7Cl$=$C^8H$— | pyrrolidine | 3,3'-biphenyl (di-CH₂ attached) | 1.20 | 0.40 | 10 |
| 7 | RSM932A | —(CH=CH)₂— | —N(Me)-C₆H₄-Cl | 4,4'-biphenyl | 2.0 | 1.2 | 12.5 |
| 8 | RSM824B | —$C^5H$=$C^6H$— $C^7Cl$=$C^8H$— | —N(Me)-C₆H₄-Cl | 4,4'-biphenyl | 11.4 | 1.2 | 15 |
| 9 | RSM936A | —(CH=CH)₂— | —N(Me)-C₆H₄-Cl | -C₆H₄-(CH₂)₂-C₆H₄- | 4.8 | 0.7 | 16.7 |
| 10 | RSMB28B | —$C^5H$=$C^6H$— $C^7Cl$=$C^8H$— | —N(Me)-C₆H₄-Cl | -C₆H₄-(CH₂)₂-C₆H₄- | 5.70 | 0.80 | 12.5 |
| EC5 | RSM1084A | —$C^5H$=$C^6H$— $C^7Cl$=$C^8H$— | pyrrolidine | -C₆H₄-(CH₂)₃-C₆H₄- | 1.00 | 0.20 | 7.5 |
| EC6 | JC/947A | H, H | —NMe₂ | -C₆H₄-(CH₂)₃-C₆H₄- | 22 | 2.5 | 0.3 |

*$R_3$ and $R_4$ can mean either each one is hydrogen or both form a single radical.

It can be observed from the data of table II that the compounds of the present invention have a considerably lower toxicity than the compounds of patent ES 2 117 950, whereas they maintain similar or greater values of antiproliferative activity against cells derived from culture tumors and of in vivo antitumor activity against human tumors inoculated in immunodepressed mice.

The invention claimed is:

1. A compound having formula I:

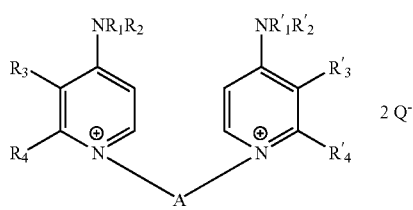

where

Q⁻ represents the conjugate base of a pharmaceutically suitable organic or inorganic acid;

$R_1$ and $R'_1$ represent, independently of each other, a radical selected from the group formed by H and $C_{1-6}$ alkyl optionally substituted by trifluoromethyl, hydroxyl or alkoxyl;

$R_2$ and $R'_2$ represent, independently of each other, an aryl radical substituted by halogen, trifluoromethyl, hydroxyl, $C_{1-6}$ alkyl, amino or alkoxyl;

$R_3$ and $R'_3$ represent, independently of each other, either a radical selected from the group formed by H, halogen, trifluoromethyl, hydroxyl, amino, alkoxyl and $C_{1-6}$ alkyl optionally substituted by trifluoromethyl, hydroxyl, amino or alkoxyl, or together with $R_4$ and $R'_4$ respectively, and independently of each other, a —CH=CH—CH=CH— radical optionally substituted by halogen, trifluoromethyl, hydroxyl, $C_{1-6}$ alkyl, amino or alkoxyl;

$R_4$ and $R'_4$ represent, independently of each other, either a radical selected from the group formed by H and $C_{1-6}$ alkyl optionally substituted by halogen, trifluoromethyl, hydroxyl, amino or alkoxyl, or together with $R_3$ and $R'_3$ respectively, and independently of each other, a —CH=CH—CH=CH— radical optionally substituted by halogen, trifluoromethyl, hydroxyl, $C_{1-6}$ alkyl, amino or alkoxyl; and A represents a spacer group having the following formula:

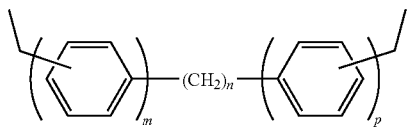

wherein m, n and p represent integers which can have the following values: m=1; n=0, 1-10; p=0, 1; with the condition that m, n and p do not take the value of zero at the same time.

2. A compound according to claim 1, wherein $R_2$ and $R'_2$ represent, independently of each other, a phenyl radical substituted by halogen, trifluoromethyl, hydroxyl, $C_{1-6}$ alkyl, amino and alkoxyl.

3. A compound according to claim 2, wherein $R_1$ and $R'_1$ represent a methyl radical, and in that $R_2$ and $R'_2$ represent, independently of each other, a phenyl radical substituted by one or more halogen substituents.

4. A compound according to claim 1, wherein both $R_3$ and $R_4$ and $R'_3$ and $R'_4$ together represent, although independently of each other, a —CH=CH—CH=CH— radical optionally substituted by one or more halogen substituents.

5. A compound according to claim 1, wherein it has the following substituents:

| No. | $(R_3, R_4)$ and $(R'_3, R'_4)$ | $NR_1R_2$ and $NR'_1R'_2$ | A | Code |
|---|---|---|---|---|
| 1 | H, H | —N(Me)—C₆H₄—Cl | (m-xylylene) | ACG560B |
| 3 | H, H | —N(Me)—C₆H₄—Cl | (biphenyl-bis-methylene) | ACG548B |
| 4 | H, H | —N(Me)—C₆H₃(Cl)₂ | (biphenyl-bis-methylene) | ACG604A |
| 5 | —(CH=CH)₂— | —N(Me)—C₆H₄—Cl | (biphenyl-bis-methylene) | RSM964A |
| 6 | —C⁵H=C⁶H— C⁷Cl=C⁸H— | —N(Me)—C₆H₄—Cl | (biphenyl-bis-methylene) | RSM820C |
| 7 | —(CH=CH)₂— | —N(Me)—C₆H₄—Cl | (p,p'-biphenyl-bis-methylene) | RSM932A |
| 8 | —C⁵H=C⁶H— C⁷Cl=C⁸H— | —N(Me)—C₆H₄—Cl | (p,p'-biphenyl-bis-methylene) | RSM824B |
| 9 | —(CH=CH)₂— | —N(Me)—C₆H₄—Cl | —C₆H₄—(CH₂)₂—C₆H₄— | RSM936A |
| 10 | —C⁵H=C⁶H— C⁷Cl=C⁸H— | —N(Me)—C₆H₄—Cl | —C₆H₄—(CH₂)₂—C₆H₄— | RSM828B. |

6. A compound according to claim 5, wherein Q represents Br (bromide) or $F_6P$ (hexafluorophosphate).

7. A compound according to claim 1, wherein it has the following substituents:

| No. | $(R_3, R_4)$ and $(R'_3, R'_4)$ | $NR_1R_2$ and $NR'_1R'_2$ | A | Code |
|---|---|---|---|---|
| 5 | —(CH=CH)$_2$— | 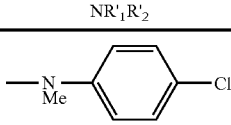 | 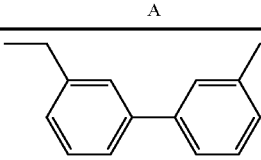 | RSM964A. |

8. A compound according to claim 1, wherein it has the following substituents:

| No. | $(R_3, R_4)$ and $(R'_3, R'_4)$ | $NR_1R_2$ and $NR'_1R'_2$ | A | Code |
|---|---|---|---|---|
| 6 | —C$^5$H=C$^6$H— C$^7$Cl—C$^8$H— | 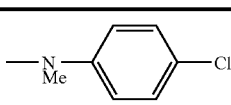 | 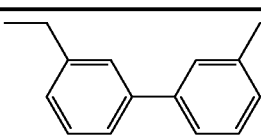 | RSM820C. |

9. A compound according to claim 1, wherein it has the following substituents:

| No. | $(R_3, R_4)$ and $(R'_3, R'_4)$ | $NR_1R_2$ and $NR'_1R'_2$ | A | Code |
|---|---|---|---|---|
| 7 | —(CH=CH)$_2$— | 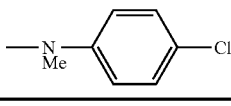 | 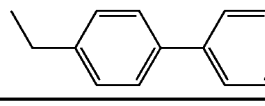 | RSM932A. |

10. A compound according to claim 1, wherein it has the following substituents:

| No. | $(R_3, R_4)$ and $(R'_3, R'_4)$ | $NR_1R_2$ and $NR'_1R'_2$ | A | Code |
|---|---|---|---|---|
| 10 | —C$^5$H=C$^6$H— C$^7$Cl—C$^8$H— | 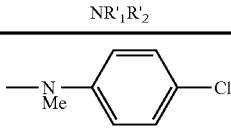 | 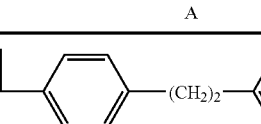 | RSM828B. |

11. A pharmaceutical composition comprising at least one compound defined in claim 1 as an active ingredient.

12. A process for preparing a compound according to claim 1 comprising reacting:

a) the corresponding heterocyclic compound of formula VII and the dihalogenated compound $AX_2$ (where X represents the halogen atom: Cl, Br or I) in 2:1 molar amounts in an organic solvent or, b) the corresponding heterocyclic compound of formula VII and the dihalogenated compound $AX_2$ (where X represents the halogen atom: Cl, Br or I) in a 1:1 molar ratio in an organic solvent, in order to give a monoquaternized product which is again reacted with another different heterocyclic molecule, in a 1:1 molar ratio, using an organic solvent that is more polar than the first one, wherein the compound having formula VII is characterized by

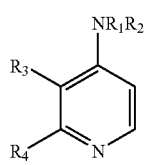

VII where $R_1$ represents a radical selected from the group formed by H and $C_{1-6}$ alkyl optionally substituted by trifluoromethyl, hydroxyl or alkoxyl;

$R_2$ represents an aryl radical substituted by halogen, trifluoromethyl, hydroxyl, $C_{1-6}$ alkyl, amino or alkoxyl $R_3$ represents either a radical selected from the group formed by H, halogen, trifluoromethyl, hydroxyl, amino, alkoxyl and $C_{1-6}$ alkyl optionally substituted by trifluoromethyl, hydroxyl, amino or alkoxyl, or together with $R_4$ a —CH=CH—CH=CH— radical optionally substituted by halogen, trifluoromethyl, hydroxyl, $C_{1-6}$, alkyl, amino or alkoxyl;

$R_4$ represents either a radical selected from the group formed by H, and $C_{1-6}$ alkyl optionally substituted by halogen, trifluoromethyl, hydroxyl, amino or alkoxyl, or together with $R_3$ a —CH=CH—CH=CH— radical optionally substituted by halogen, trifluoromethyl, hydroxyl, $C_{1-6}$ alkyl, amino or alkoxyl.

13. The compound according to claim 12 having formulas: 4-(4-chloro-N-methylanilino)quinoline

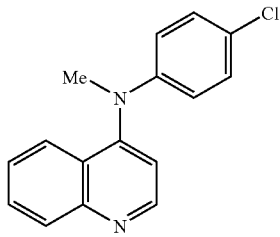

VIII A and 7-chloro-4-(4-chloro-N-methylanilino)quinoline

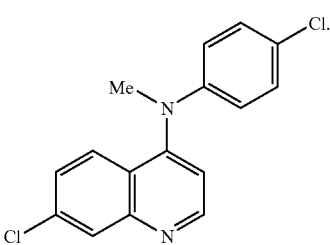

VIII B

14. A method for treating colorectal cancer in a patient in need of such treatment, said method comprising administering a compound according to claim 1.

* * * * *